United States Patent [19]
Ikariyama et al.

[11] Patent Number: 5,256,271
[45] Date of Patent: Oct. 26, 1993

[54] METHOD OF IMMOBILIZING BIOFUNCTIONAL MATERIAL, AND ELEMENT PREPARED THEREBY, AND MEASUREMENT BY USING THE SAME ELEMENT

[75] Inventors: Yoshihito Ikariyama, Tokorosawa; Shigeru Yamauchi, Tokyo; Tomoaki Yukiashi, Funabashi, all of Japan

[73] Assignees: Japan as represented by President of National Rehabilitation; Sumitomo Cement Co., Ltd., both of Japan

[21] Appl. No.: 714,901

[22] Filed: Jun. 17, 1992

Related U.S. Application Data

[63] Continuation-in-part of Ser. No. 294,660, Mar. 11, 1989, which is a continuation of Ser. No. 492,849, Mar. 13, 1990.

[30] Foreign Application Priority Data

Mar. 17, 1987 [JP] Japan .................................. 62-55387
Dec. 3, 1987 [JP] Japan ................................ 62-304524

[51] Int. Cl.$^5$ ............................................. G01N 27/26
[52] U.S. Cl. .................................. 204/403; 435/817; 435/176; 435/288; 435/291
[58] Field of Search .................... 204/153.12, 403, 16, 204/47; 435/176, 288, 291, 817

[56] References Cited

FOREIGN PATENT DOCUMENTS 2215861 3/1986 Japan .
1107050 2/1982 U.S.S.R. .
2191003 12/1987 United Kingdom .

Primary Examiner—John Niebling
Assistant Examiner—Bruce F. Bell
Attorney, Agent, or Firm—Hoffman, Wasson & Gitler

[57] ABSTRACT

A microbioelectrode having high performance produced by immobilization by incorporating a biologically active substance in the interior or on the surface of a porous conductive material layer or fine particle layer which has been deposited on the surface of a transducing material. The inventive microbioelectrode demonstrates sufficient output even if the sensor using the electrode is very small in size.

20 Claims, 11 Drawing Sheets

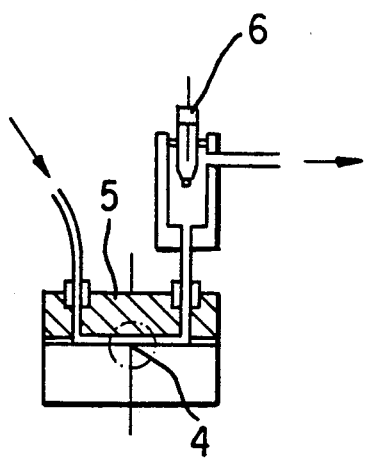
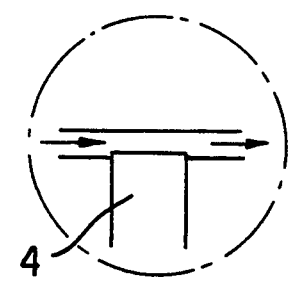
FIG. 4A  FIG. 4B
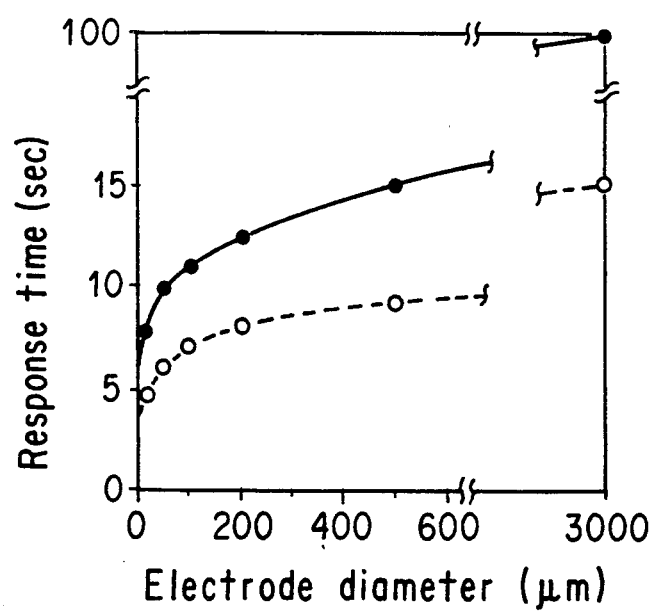
FIG. 5

METHOD OF IMMOBILIZING BIOFUNCTIONAL MATERIAL, AND ELEMENT PREPARED THEREBY, AND MEASUREMENT BY USING THE SAME ELEMENT

CROSS-REFERENCE TO RELATED APPLICATION

This is a continuation-in-part of U.S. patent application Ser. No. 07/294,660 filed on Mar. 11, 1989, which is based on International Application Serial No. PCT/JP88/00256 filed on Mar. 11, 1988 and which designated the United States.

Further, this is a continuation of U.S. patent application Ser. No. 07/492,849 filed on Mar. 13, 1990.

FIELD OF THE INVENTION

The present invention relates to a microbioelectrode having high performance, and a method of manufacturing the same. Particularly, it relates to a method for preparation of a microbioelectrode having a diameter in the order of micrometers, which can enable one to manufacture an analytical instrument with high performance to secure real time measurement.

DESCRIPTION OF THE PRIOR ART

Biosensing electrodes made predominantly of an immobilized enzyme and transducing electrode are well-known in the prior art. Recent attempts for the construction of such electrodes have been made by immobilizing an enzyme on various transducing electrodes.

Hitherto, enzymes have been immobilized on supporting matrices by covalent coupling, physical adsorption or ionic binding. Most of the conventional supports have been made of polymeric membranes. These conventional enzyme membranes have been attached to the surfaces of transducing electrodes, e.g. oxygen electrodes or hydrogen peroxide electrodes.

Further, details of such techniques can be found in the book entitled "Biosensors Fundamentals and Applications", edited by A. D. F. Turner, I. Karube and G. S. Wilson; published from Oxford University Press, in 1988.

The use of immobilized enzymes in membrane form as the receptor materials for biosensing devices has produced convenient analytical instruments, whereby a physiologically active substance can be easily detected and measured with high sensitivity and high selectivity. However, the preparation of such membranes has heretofore been time-consuming. Furthermore, such techniques are not readily adopted to fabricate miniaturized biosensors having diameters in the micrometer order.

There has arisen a need for a method of preparing an enzyme-embodied electrode, i.e., an enzyme and electrode can be combined, so as to produce a microbioelectrode with high performance, wherein physiologically active substances can be determined with high accuracy and sensitivity.

Many attempts have been made to conquer these problems, as described below.

Keyes (U.S. Pat. No. 3,839,175) patent discloses a process for electrolytically depositing and immobilizing an enzyme by inducing electrolytic migration of the enzyme in an aqueous dispersion thereof, and intercepting the migrating enzyme on an inert inorganic, porous, sorptive, dimensionally stable, fluid permeable supporting matrix to form a biologically active composite, where the supporting matrix is ceramic and has been formed by compacting and sintering refractory oxide powders such as alumina.

Freeman et al (U.S. Pat. No. 4,659,665) discloses a membrane or film containing a biologically active protein such as an enzyme, which is prepared from a polymer substituted with acyl hydrazide groups, preferably an acrylamide/-methacrylamide copolymer in a given respective molar ratio, with acryl hydrazide group substitution, and the membrane being formed on an electrode, and crosslinked with a crosslinking agent to produce an enzyme electrode.

Japanese Patent Publication No. 84-052598 discloses fixing of enzymes on a polymer matrix, which matrix is set between two electrodes or envelopes of the electrodes. When a voltage of, preferably, 10 to 500 V is applied between the electrodes, the enzyme will move in the solution on electrophoresis and is fixed in the polymer. The similar proposal is disclosed in Japanese Patent Publication No. 84-11186. In the above-mentioned two patents, the matrix is placed on the insulating material, and the electrode and the supporting material are of different material.

Further, Japanese Patent Publication No. 87-304424/43 discloses use of protein coated magnetic particles as a carrier for securing an enzyme on the electrode. Therefore, the carrier is not conductive.

Japanese Patent Publication No. 85-259356 discloses that an aluminum base is subjected to anodic oxidation with a high current density of 5 to 60 A/cm$^2$ in an acidic solution to form an anodic oxide film on the surface, and then immersed in a buffer solution containing an enzyme so as to adsorb the enzyme on the carrier comprising a barrier layer (280 to 300 Angstrom), a porous layer (53 micrometers) and a needle-like constitution layer (31 micrometers) formed on the base.

In those prior art electrodes, the electronic reaction and enzymatic reaction are carried out in separate places. In other words, the electrode and the media in which the enzymatic reaction takes place or occurs are separated, and therefore, are not integrated. Therefore, high speed measurement cannot be expected, and miniaturization of the device is difficult.

SUMMARY OF THE INVENTION

With the foregoing considerations in mind, the present invention contemplates the provision of a microbioelectrode and a method for preparation of the same. Such microbioelectrode can be assembled in a new sensing device to determine physiologically active substances.

It is an object of the present invention to provide an efficient and sensitive microbioelectrode and a method for the preparation of the same.

It is another object of the present invention to provide a new type of an electrode structure which can be miniaturized to the order of micrometers, and can function as a sensitive electrode to detect physiologically active substances which can be recognized with a biologically active substance, which is maintained in the microbioelectrode.

It is a further object of the present invention to provide a new method of preparing a sensitive, miniaturized electrode with rapid detection of a physiologically active substance.

Throughout the specification, the below listed terms are used to mean the following terminology.

"Transducing electrode" means "an electrode where enzyme-generated electrochemically active species are converted to generate an electric signal".

"Enzyme-embodied electrode" means "a porous transducing electrode in which enzyme molecules are directly immobilized, consequently a biochemical reaction and an electrochemical reaction can occur simultaneously therein".

"Microbioelectrode" prepared in accordance with the present invention means "an electrode having a diameter to the level of the micrometer order, preferably in the range from 1 micrometer to several millimeters, and which has a porous conductive layer incorporating 'biologically active substance(s)' immobilized therein".

"Biologically active substances" means "substances to be immobilized or incorporated in a porous conductive layer formed on the surface of a transducing electrode employed for the fabrication of the microbioelectrode of the present invention". "Biologically active substance" may include an enzyme, antibody, organelle, microorganism, and/or binding protein.

"Physiologically active substances" may include "intermediate metabolites, hormonic substances and tumor-related markers, which can be determined by the inventive microbioelectrode".

BRIEF DESCRIPTION OF THE DRAWINGS

FIGS. 4A and 4B shows schematically the structure of an electrode assembly transducing cell using the inventive microbioelectrode as a detector, for a flow injection analysis.

FIG. 5 shows the relation between response time and the diameters of the inventive microbioelectrode in measuring response current in a flow measurement of a glucose containing solution.

DETAILED DESCRIPTION OF PREFERRED EMBODIMENTS

Figure 1A:
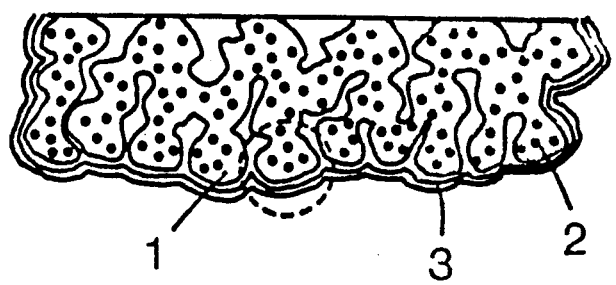
FIGS. 1A and 1B show schematically a sectional view of the microbioelectrode by the present invention, and the magnified view of the encircled portion, showing the detailed structure of porous conductive layer in which enzymes are incorporated and immobilized.

The inventors have found that a biologically active substance can be immobilized in the interior or on the surface of porous conductive material layer or fine particle conductive layer on the surface of a conductive material, by depositing very fine conductive particles or a porous conductive layer on the surface of a transducing material, and then, immersing such conductive particle layer or porous conductive layer in a solution containing biologically active substance(s) or alternatively further followed by stabilizing the incorporated biologically active substance(s) with a crosslinking agent.

In the method of fabrication of the inventive microbioelectrode, the conductive material to be used as transducer matrix, that is, the conductive material of the layer is not necessarily the same as the base conductive material for the electrode.

For example, the combination of platinized platinum (platinum black) on the surface, e.g. of the edge of a platinum wire can be preferably used wherein the platinized platinum or platinum black is deposited on the surface by treating electrolytically the surface of the platinum in a solution containing a platinum complex. However, another porous conductive material such as gold black, particulate rhodium oxide, particulate ruthenium oxide ($RuO_3$), palladium black, or iridium black can be deposited or formed in place of the platinum black on the surface of the edge of a platinum wire so as to produce the inventive microbioelectrode. Any material which can form a conductive layer of fine particular material on the conductive surface of a base for an electrode can be used.

Further, the other conductive material such as gold wire, silver wire and the other metal wire can be used as a base transducing material for the inventive microbioelectrode in place of the platinum wire.

Because such conductive porous layer is formed on the conductive base surface as mentioned above, the inventive microbioelectrode has a surface area of several thousands times that of the apparent surface area, and further, has a high selectivity to the substance(s) to be detected, with high S/N ratio due to the sufficient amount of immobilized enzyme within the porous electrode matrix (layer) of the inventive microbioelectrode.

This high S/N ratio of the measured values measured by application of potential to the inventive microbioelectrode meets the requirement of high sensitivity to the physiologically active substance to be detected, with a wider dynamic range. The inventive microbioelectrode can demonstrate sufficient output even if the sensor using this electrode is very small size, because the actual surface area thereof is much higher than what is expected from its apparent size. Therefore, the amount of the sample required for the measurement of the response output can be very small, and, the analytical apparatus using the inventive microbioelectrode can be easily miniaturized, i.e. the desired microinstrumentation can be easily produced. The advantages of the analytical apparatus being in small size are supported in a batch system measurement as well as in a flow injection analysis. Further, the analytical apparatus using the inventive microbioelectrode is advantageous in rapid response, high sensitivity and high resolution with wide dynamic range. Further, the inventive microbioelectrode can be used and assembled in a rapid biosensing device which can detect a target substance within a few milliseconds even when using trace droplet samples.

It has been known that an electrode with platinized platinum having very high surface area can have high catalytic activity for hydrogenation. However, the incorporation or immobilization of biologically active substance(s) in such platinized platinum layer has not been known.

While it has been known to immobilize an enzyme and the like in the pores of platinum, which pores are fabricated by etching, and then bind the enzyme on the surface of the platinum with a crosslinking agent, those porous surfaces have only several $m^2/g$ of surface area in an ordinary condition, for example, as disclosed in Japanese Laid-open Patent Application No. 57-107,764. Further, it has been known that the size of platinized platinum pores can be controlled so as to incorporate biologically active substance(s) in the pores.

In accordance with the present invention, biologically active substances can be immobilized or directly unitized among the fine porous particles of an electrically conductive material, so as to fabricate a new type bioelectrode having incorporated therein biologically active substance(s) on or among the fine porous particles of the conductive material.

This can be performed, for example, by immersing the finely porous metal layer formed on the small surface of a conductive material in an aqueous solution of a biologically active substance, and alternatively if necessary, stabilizing the immobilized active substance with a polymeric material such as albumin or heparin so as to prevent any trace dissolution of the active substance from the conductive porous layer. Further, the immobilized substance can be insoluble with a crosslinking agent so as to form an insoluble crosslinked substance on the conductive porous layer. Therefore, the method of immobilizing the biologically active substance on or among the fine particles of the conductive layer in accordance with the present invention can be applied to the whole immobilization of enzymes in a molecular form.

Further, a film can be formed on an active substance immobilized layer having a thickness of several thousand Angstroms or less, and therefore, the presence of the film does not affect the activity of the immobilized biologically active substance incorporated in the porous conductive layer.

Polymeric material(s) which can be used for covering the surface of the microbioelectrode in accordance with the present invention may include proteins such as albumin, and polysaccharides such as heparin.

The usable crosslinking agent in accordance with the present invention is preferably a crosslinking agent adopted for the biologically active substance. The usable crosslinking agent may include glutaraldehyde, carbodiimide and maleinimide coupling agents.

Further, an electron mediator such as ferrocene can be incorporated in the fine particle conductive layer with a biologically active substance, so as to enable measuring a target determinant even in the absence of dissolved oxygen or with less oxygen, otherwise oxygen has to be dissolved in a solution containing a target analyte. Further, the presence of mediator in the porous conductive layer formed in accordance with the present invention enables one to reduce significantly the potential necessary for the measurement of the target substance by using the inventive microbioelectrode. Such further treatment of the microbioelectrode with mediator may reduce the influence of concomitant oxidizable substances such as ascorbate and uricate.

Figure 1B:
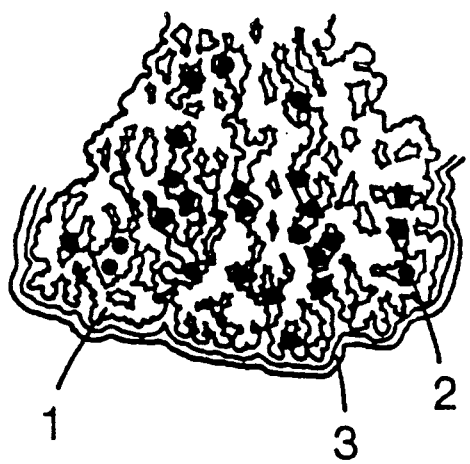

The structure of the conductive porous layer formed on the conductive base in accordance with the present invention is shown in FIGS. 1A and 1B, showing the incorporation of a biologically active substance immobilized therein. As shown in the drawings, the active substance is incorporated on or among the conductive fin particles in the layer. For example, the platinum fine particles (platinum black) layer, as deposited electrically on the surface of an electrode base, and incorporating the active substance among the particles cannot be easily peeled off even when the microbioelectrode is vigorously agitated in a solution, and is maintaining the activity of the incorporated and immobilized biologically active substance such as an enzyme.

The active substance can be crosslinked so as to stabilize the active substance in the pores of the layer. Further, the enzyme-incorporated platinum black layer can be coated with polymeric material such as albumin.

Recently, Polta and Johnson have proposed the electrochemical determination of electro-inactive species in the article, Analytical Chemistry, 59 at pages 204 to 207 (1985). They employed the formation of surface oxide on the surface of a metal electrode for the determination of carbohydrates and amino acids. In their proposal, non-specific response to the determinant was utilized.

In contrast, in the microbioelectrode of the present invention, the selectivity on the measurement of a target can be improved by anodically polarizing the microbioelectrode.

An analytical instrument which can be fabricated by using the inventive microbioelectrode will be developed in a miniaturized size but have rapid response and high sensitivity. This feature is extremely important for the development of a clinical analyzer or a downstream analyzer that requires miniaturization of a biosensor with multiple functions.

The inventive method of immobilizing an active substance in an electrode will develop a special electrode which is characterized by whole incorporation of active substance such as enzyme and antibody without any effect to the active substance due to intact immobilization.

The inventive microbioelectrode provides: 1) highly sensitive detection, 2) rapid response, 3) sufficient life time and 4) reliable reproducibility. Such high performance of an electrode can be obtained mainly from the high density of the immobilized active substance in the very fine particles (platinum black) of the deposited layer formed on the surface of conductive material.

The inventive microbioelectrode is advantageous in the low S/N ratio, because it has very large surface area amounting to much higher orders of the magnitude than the apparent surface area, which can be fabricated by the deposition of conductive fine particles on the flat surface of a conductive base.

An analytical instrument which can be manufactured by using the inventive microbioelectrode will evidence high performance such as highly rapid response and high sensitivity, which can be found preferably in both batch analysis and flow injection analysis. Further, the inventive technique will provide a biological analytical system with high resolution and stability, because the inventive microbioelectrode incorporates stably a biologically active substance therein.

In batch system measurement, a linearity between generated current (or the current value at the certain time) and concentration of a target substance (or glucose for example) is found or can be established in the range from 0.5 micro moles (mol/1) to 50 mM (millimoles). Because the present invention employs electrochemical technique and the inventive microbioelectrode is fabricated by the deposition of conductive fine particles or conductive porous layer, the inventive microbioelectrode may be in any form, and preferably, in disc, spherical or tubular form. Further, the inventive microbioelectrode can be very small in size, and therefore, the sample to be measured can be in an extremely small amount even for the measurement of a target substance in very low concentration. Further, very high speed measurement can be enabled, i.e., several hundred samples per one hour can be dealt in a continuous flow measurement.

The inventive microbioelectrode can be assembled in an array, which facilitates multifunctional measurement of multiple components in one sample at the same time in a flow analysis or in a batch analysis.

One of the biosensors using the inventive microbioelectrode can be a real time measuring device which has three electrodes including the inventive electrode assembled in a small size device, and therefore, can be operated by a pulse potential application mode. Then, droplet stationary samples can be loaded on the sensing device using the inventive microbioelectrode. The output generated in the sensor by using the microbioelectrode is taken in a few milliseconds for the measurement of a target substance, e.g. droplet samples containing glucose is loaded on the sensing device where a glucose oxidase immobilized microbioelectrode in accordance with the present invention, a counter electrode and an Ag/AgCl reference electrode are assembled on a tip of a Teflon -type casing.

The inventive microbioelectrode can be used so as to enable measuring very small amounts of a sample, e.g. a droplet sample of only one microliter.

After a very small amount of sample is loaded, a potential is applied to the electrode, and the generated current thereby is detected, and then, the concentration of the target substance in the sample can be determined from the height of the current.

The active substance (e.g. glucose oxidase) incorporated in the porous layer of the inventive microbioelectrode will react with a target substance (e.g. glucose) by applying a potential to the electrode, so as to generate an electroactive species in the electrode, thereby generating a current in the electrode, which current can be detected by a recorder. Therefore, the current can be detected in real time by pulse potential application mode.

Various pulse application modes can be used to detect the current using the inventive microbioelectrode, and further a sample can be measured even in a stationary state. Because the bioanalytical system using the inventive microbioelectrode can detect directly the active species generated in the electrode, any of bioactive substances, such as oxidizing enzymes and dehydrogenating enzymes can be employed as a biologically active substance in the conductive porous layer of the electrode.

The inventive method of immobilizing a biologically active substance in the porous layer of the electrode can provide unique enzyme electrodes such as the ones described herein. An analytical system or method for measurement with microbioelectrode is advantageous in high performance such as rapid response and high sensitivity, and further, can provide an in vivo biosensing system and a portable biosensor, and can be further applied to a potentiometry-based biosensor.

In carrying out the present invention, three modes of applying immobilized biologically active substance(s) by using an inventive microbioelectrode are illustrated. In describing these modes, glucose oxidase is taken as a typical example of a biologically active substance to be immobilized in the porous conductive layer, and glucose is to be determined by the inventive microbioelectrode.

A transducer base to be used for the formation of very fine particle layer or porous conductive layer on its surface can be platinum wire having a diameter below one micrometer. The fine particle layer or porous conductive layer is formed by electrolytically depositing the conductive material (e.g. platinum black) on the surface from a solution containing a platinum complex, and preferably further a trace amount of lead ion. Then, the particular conductive layer is immersed in a solution containing a biologically active substance, e.g. enzyme, so as to be immobilized in the layer. Further, the enzyme molecules in the layer can be crosslinked by a bifunctional coupling agent, to ensure stability of the immobilized enzyme thereby, enabling them to have long lifetime for the resulting microbioelectrode of the present invention.

Any electrically conductive material such as metal, carbon and conductive polymers can be used as a base conductive material for the inventive microbioelectrode. Suitable material for the base of the electrode may be metallic substances such as platinum, gold and graphite. When the material for the base is metal, the suitable form is preferably wire, or pin.

The porous layer or very fine particle layer can be prepared on the surface of the base material. The material of the layer is electrically conductive and preferably is a particular porous layer which can be electrochemically deposited on the surface of the conductive material, so as to form such fine particle layer or porous layer.

Suitable materials for the layer may include platinum black, gold black, palladium black, iridium black, rhodium oxide, ruthenium oxide ($RuO_3$), conductive polymer and graphite.

Either potentiostatic or galvanostatic deposition of conductive fine particles can be used to form such layer on the surface of the conductive base. Potential and current requirements are dependent on the metal complex and geometrical parameters of the base for the electrode. Generally speaking, it is preferable to use a relatively low voltage supply for deposition of conductive particle layer, in the case of potentiostatic deposition, such as from about minus 0.1 to minus 0.2 volts versus an Ag/AgCl electrode. When galvanostatic deposition is used to form the layer, one should pay attention to the drastic change in pH in the vicinity of the electrode. The time required for immobilizing enzyme in the micropores of the layer is mainly dependent on the enzyme concentration.

Referring now to FIG. 1, a porous layer 1 of conductive material, or a layer of conductive and very fine particles is electrochemically formed or deposited on the surface in very small size of conductive material base, and further, a thin polymer film 3 is formed on the surface of the porous transducer matrix 1 (or the layer 1) of the electrode, wherein enzyme 2 can be stabilized chemically.

The enzyme electrode (microbioelectrode), a counter electrode and a reference electrode are immersed in a solution to be measured, and followed by applying a potential of 0.6 V versus the Ag/AgCl reference electrode. As soon as the background current reaches a steady state current, a glucose sample is added. The current generated upon the addition of glucose is a sensor response in a batch system measurement.

An electrode assembly for flow measurement is shown in FIG. 4, wherein an electrode 4 of the present invention is assembled in a thin layer cell along the passage for the sample, and a stainless steel upper cell 5 used as a counter electrode is assembled as shown in the drawings, and Ag/AgCl electrode 6 is positioned at the downstream along the passage of the sample. A glucose sample can be repeatedly injected to a mobile buffer to pass through the passage.

Figure 9:
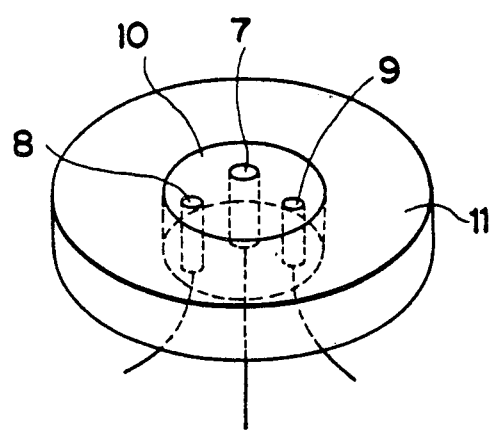
FIG. 9 shows a schematic view of planar sensing cell using the inventive microbioelectrode with three electrode measurement system, where pulse voltammetric potential is applied to the electrode as shown in FIGS. 1A and 1B.

The other type of electrode assembly for measurement by the application of voltammetric pulse is shown in FIG. 9. An electrode 7 of the present invention, a counter electrode 9 and an Ag/AgCl reference electrode 8 are assembled into a biological sensing device, wherein a trace droplet sample is loaded for the pulse voltammetric or chronoamperometric measurement.

In addition, anodic polarization treatment of the resulting microbioelectrode can enable to improve the selectivity to a physiologically active substance or a target substance. In other words, formation of surface oxide on the microbioelectrode makes the sensor reliable selectivity.

The present invention is illustrated in detail by the following examples, but such examples should not be interpreted for the limitation of the invention.

EXAMPLE 1

Fabrication of a Biologically Active Substance Immobilized Electrode (Microelectrode)

A platinum wire having a diameter of 50 microns was sealed in a soda glass tubing, and the end surface of the wire was polished with alumina powder to form a clean, flat end surface for a platinum electrode. The resulting surface was electrochemically cleaned for 30 minutes in a bath of 0.5 molar sulfuric acid solution, using a silver/silver chloride electrode as a reference electrode. The potential applied to the platinum electrode was scanned between 1.3 V and minus 0.25 V at a scanning rate of 100mV/sec.

Platinum deposition was carried out for 10 minutes in a solution of 3% hexachloroplatinate containing 300 ppm of lead acetate at the current as listed in Table 1 to form platinized platinum black.

The formed platinum black layer was about several micrometer thick.

Then, the resulting platinum black electrode was dried at 25° C for 60 seconds by blowing air, and was immersed in a solution containing 5,500 units of glucose oxidase so as to immobilize glucose oxidase in the platinum black layer of the electrode.

Then, the electrode was maintained for 10 minutes in 1 milliliter of phosphoric buffer solution (pH=6.8) containing 1% of glutaraldehyde as a crosslinking agent for the glucose oxidase. The porous layer was immersed further for 10 minutes in one milliliter of phosphoric buffer solution containing 10% of albumin, and then treated with the bifunctional agent to prepare an albumin thin film over the surface of the porous layer. The resulting electrode was washed overnight in a 0.1 M buffer solution of phosphoric acid.

The response property of the resulting electrode of the present invention was evaluated in a buffer solution of phosphoric acid of an electrochemical cell where a reference electrode, a counter electrode and the microbioelectrode as a working electrode were employed in a three electrode system.

Each of those electrodes were connected respectively to a potentiostat. A potential of 0.6 volts was applied to the microbioelectrode versus the reference electrode, and then, glucose was added, and the resulting oxidation current was measured.

Figure 2:
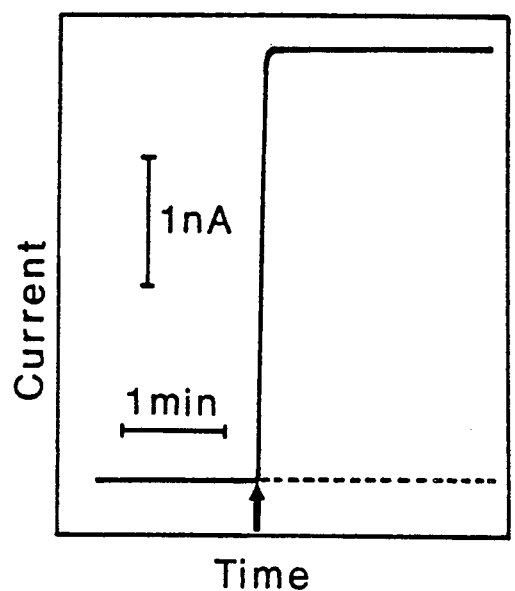
FIG. 2 shows a response curve measured by using the inventive microbioelectrode incorporating glucose oxidase responsive to glucose in a batch system measurement.
Figure 3:
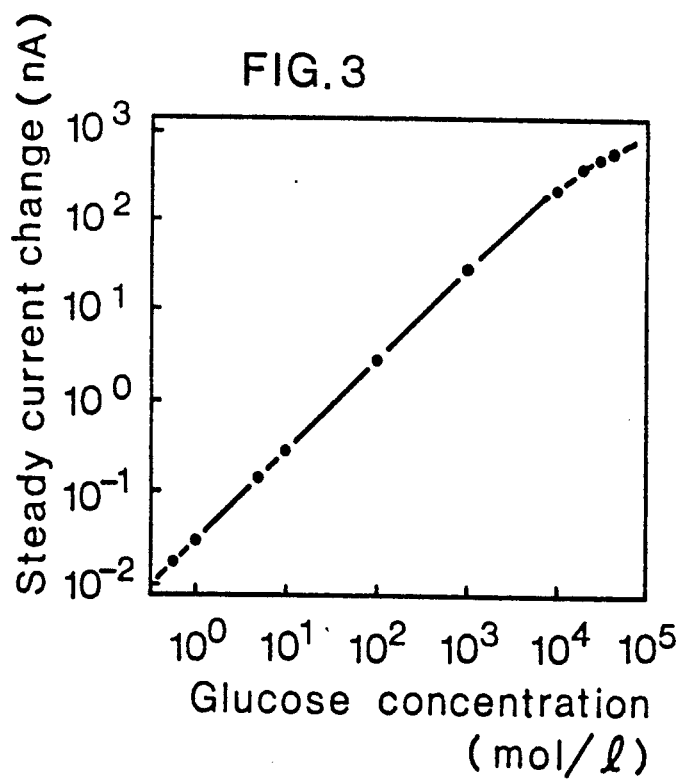
FIG. 3 shows the relation between microbioelectrode output and glucose concentration measured by using the inventive microbioelectrode having glucose oxidase, in a batch system measurement, wherein a potential of 0.6V versus Ag/AgCl electrode is applied to the solution containing glucose.

The microelectrode showed 100% response within three seconds (FIG. 2). As shown in FIG. 3, it evidences that the inventive microbioelectrode can measure even in the order of 0.1 mg/dl, and the current increases linearly at a concentration range from 0.1 mg/dl to 100 mg/dl.

EXAMPLE 2

Relation between the size of Electrode and the sensitivity

The potential for platinum deposition was minus 0.17 volts versus the reference electrode. The deposition period for immobilization was 5 minutes in every microbioelectrode.

Microbioelectrodes of various sizes were fabricated. Then, the fabricated microbioelectrodes were evaluated in terms of responsiveness, response ability and detectable range. The result is shown in Table 1.

TABLE 1

| Fabrication Condition | | Characteristics of Electrode | | | |
|---|---|---|---|---|---|
| Electrode Size (micrometer) | Peak Height of Wave (microampere) | Response to 1 mM/mM (nA) | Detectable Range (M) | Km (mM) | CV(N) % |
| 1 | 1 | 0.5 | $10^{-4}$–$10^{-2}$ | 80 | 5.0(10) |
| 10 | 7 | 5.0 | $10^{-5}$–$5 \times 10^{-2}$ | 60 | 2.5(10) |
| 50 | 20 | 29.2 | $5 \times 10^{-7}$–$10^{-2}$ | 45 | 1.5(20) |
| 200 | 65 | 166 | $5 \times 10^{-7}$–$10^{-2}$ | 35 | 0.8(20) |
| 500 | 105 | 278 | $5 \times 10^{-7}$–$10^{-2}$ | 30 | 0.6(20) |

The first column indicates the size of the electrode in micrometers, i.e. the diameter of platinum wire. The second column indicates the peak height of $H_2$ adsorption wave by a cyclic voltammetry in microamperes. The third column indicates one of the properties of the fabricated microbioelectrode, the mean response to 1 mM glucose in nanoamperes. The fourth column indicates the detectable range of the concentration of glucose in moles. The fifth column indicates Michael's constant, Km in unit of mM. The last column indicates the coefficient of variation (%) in glucose response determination.

Using the fabrication condition shown in Table 1, the platinated platinum layers were deposited on the edge surface of platinum wires having eh sizes as shown in Table 1, for 5 minutes in every electrode, and then, the sensitivity and the dynamic range were measured as shown in Table 1.

In the above-mentioned preparation of the microbioelectrode of the present invention, the potentiostatic deposition of conductive fine particles was used to form such layer on the surface of the conductive base.

Galvanostatic deposition can be alternatively used.

EXAMPLE 3

Flow Injection Analysis using the Microbioelectrode

Figure 7:
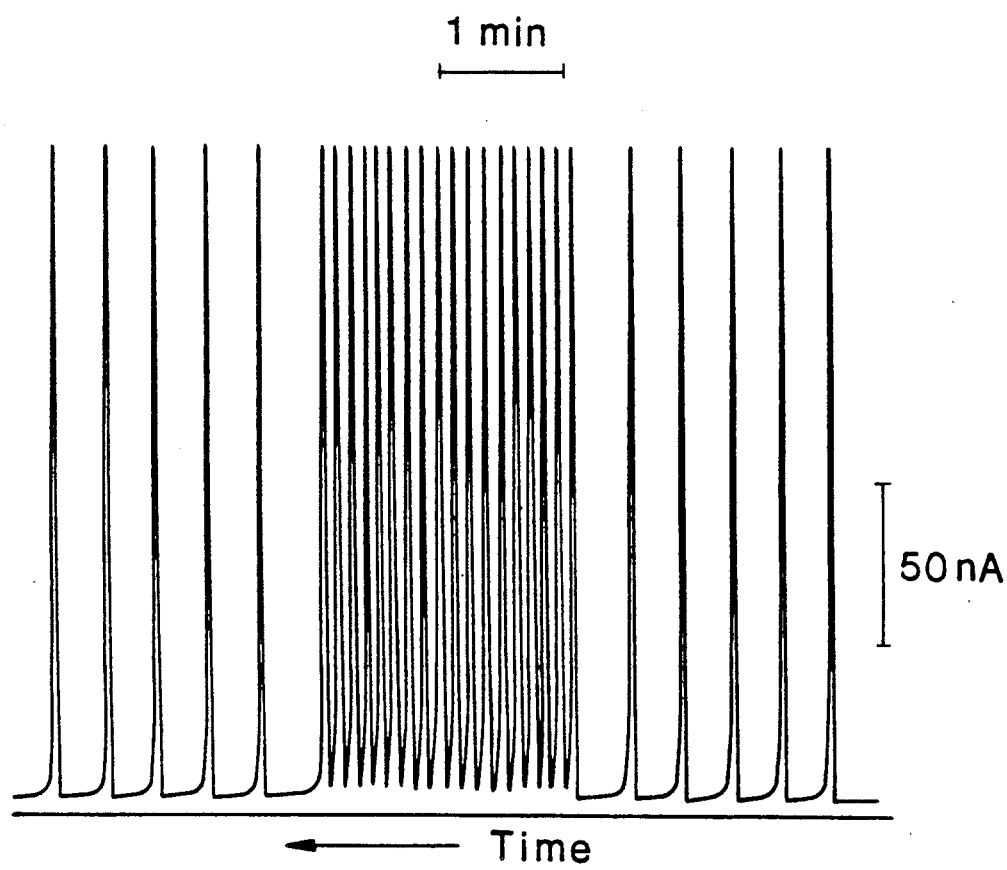
FIG. 7 is a graph showing repeated response measured by using the microbioelectrode in a flow injection measurement.

A microbioelectrode having a diameter of 100 micrometer was assembled in a thin-layer transducer cell (FIGS. 4A and 4B) for a flow injection analysis, and was used to measure the peak height current corresponding to the known concentration of glucose. The typical response is shown in FIG. 7. Approximately 10 samples per one minute were injected to the flow injection analysis.

Figure 6:
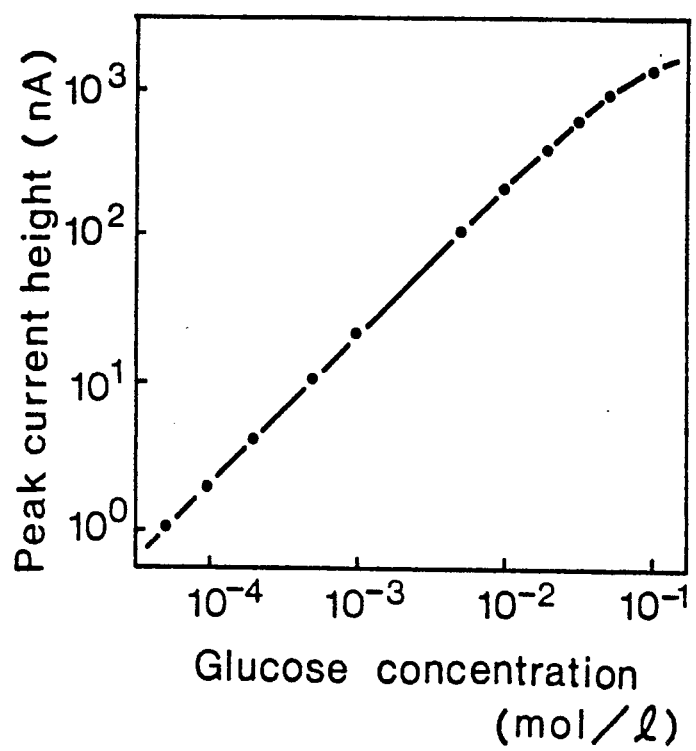
FIG. 6 is a graph showing the relation between glucose concentration in the solution and response output measured by using the inventive microbioelectrode in a flow injection measurement.

A series of glucose samples were prepared and injected into the assembled cell for the flow injection analysis, and then the peak current was measured. The resulting peak height was plotted against glucose concentration as shown in FIG. 6.

An aliquot of glucose sample (10 microliter) containing 10 mM glucose was repeatedly injected to the assembly of FIGS. 4A and 4B using the inventive microbioelectrode, so as to determine coefficient of variation in the flow injection measurement. Six hundred aliquots were injected in one hour, and then the current generated was measured. The coefficient of variation for 600 samples was less than one percent. Excellent coefficient of variation was obtained by the assembly of FIGS. 4A and 4B, using the inventive microbioelectrode.

EXAMPLE 4

Relation between Electrode Size and Response Time

A variety of the microbioelectrodes were assembled in a thin-layer transducer cell as illustrated in FIGS. 4A and 4B.

FIG. 5 shows the relation between the electrode size and the response time. The solid line indicates a time necessary to return to the base current. The broken line denotes the shortest time that successive and intermittent injections do not interfere with each other as shown in FIG. 5. It is apparent that one of the advantages is the smallness of the electrode, i.e., the smaller the electrode, the faster the response.

EXAMPLE 5

Life time and Stability of the Microbioelectrode

Figure 8:
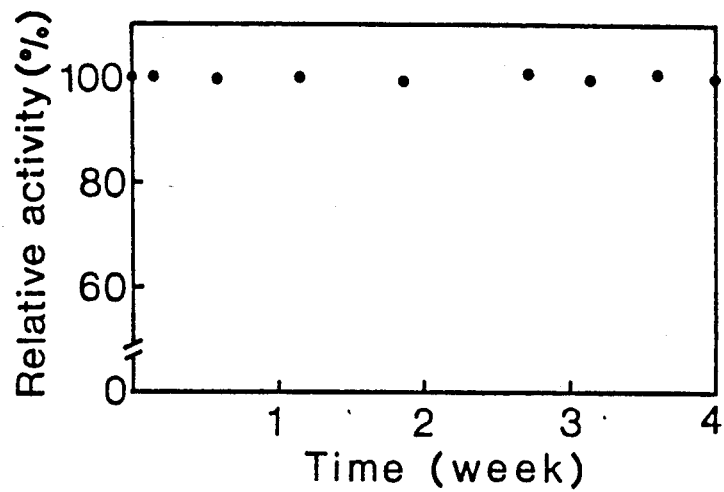
FIG. 8 is a graph showing the time stability of the current value measured by using the inventive microbioelectrode in a flow injection measurement, where one hundred samples are injected in each point.

The measurement of glucose sample was continued for one month by injecting samples repeatedly to the assembly of FIGS. 4A and 4B. The response was recorded, and the result is shown in FIG. 8. Each point represents one hundred samples injected at room temperature. This assembly was stored in a refrigerator when not in use.

EXAMPLE 6

Microbioelectrode for Transient Response Mode Analysis

The inventive microbioelectrode 7 having a diameter of 50 micrometers, a counter electrode 9 and an Ag-/AgCl reference electrode 8 were assembled in a biosensing device as shown in FIG. 9.

Figure 10:
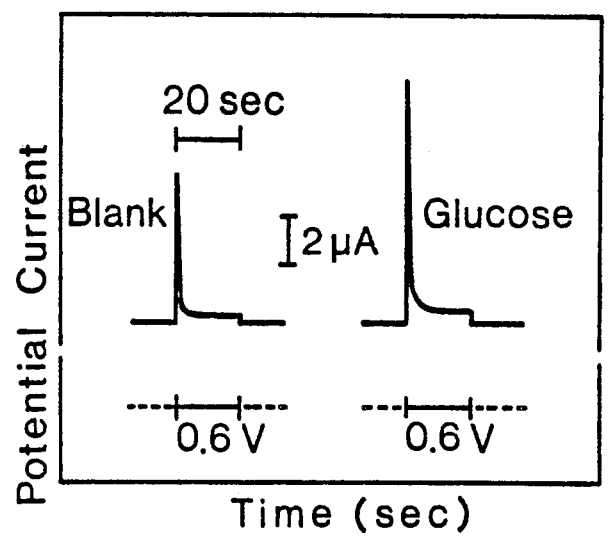
FIG. 10 is graph showing the current generated when the constant potential is applied to the sensing cell using the inventive microbioelectrode as shown in FIG. 9, wherein the response curves were measured by an X,t-recorder with response time of 200 milliseconds.

After loading a droplet (10 microliter) of sample containing 10 mM of glucose, a potential of 0.6 V versus Ag/AgCl reference electrode was applied to the device by a potentiostat. The transient output of the biosensing device was recorded with an X-t recorder of 200 microseconds response time. A phosphate buffer solution of 0.1 M was taken as a blank sample. The response curves for a blank sample and a glucose sample were shown in FIG. 10.

Figure 11:
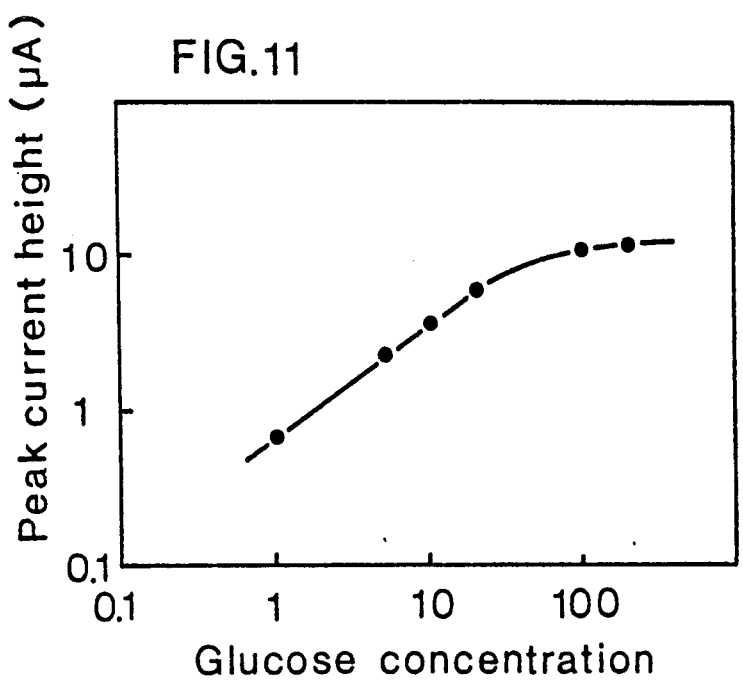
FIG. 11 is a graph showing the relation between the current generated by the inventive microbioelectrode and the glucose concentration in the solution, as measured in the sensor of FIG. 9.

Next, a series of samples having different glucose concentrations were loaded on the device of FIG. 9 to measure the output response current. The differences between the peak current for the predetermined glucose concentration and that for a blank were plotted in a graph of FIG. 11.

EXAMPLE 7

Dependence of Transient Response on Sample Volume

Figure 12:
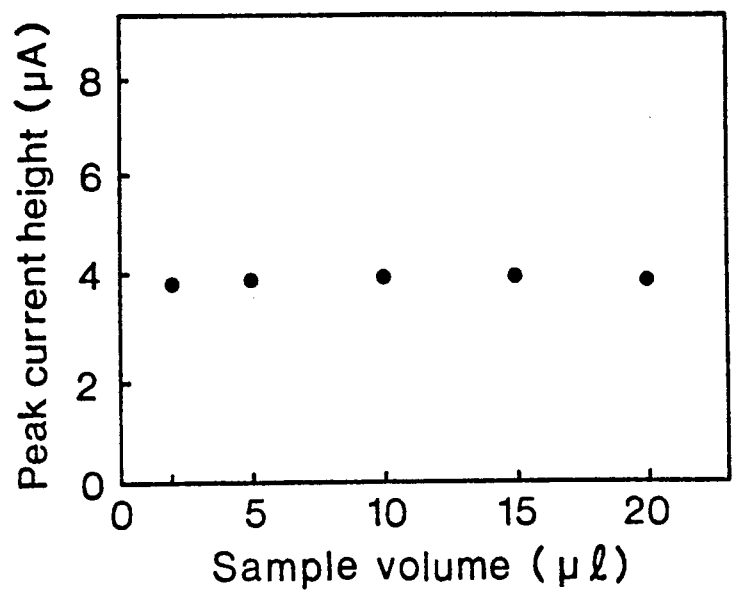
FIG. 12 is a graph showing the relation between the sample volume be used for the measurements, and the peak current measured by the pulse voltammetric measurement using the inventive microbioelectrode, in the devices as shown in FIG. 9.

A series of droplets of glucose of 10 mM samples having different volume were loaded on the device of FIG. 9 to measure transient response current. The difference in peak height between glucose concentration and a blank is shown in FIG. 12. The result shows the advantage of the present biosensing device using the inventive microbioelectrode, over conventional apparatuses, which require additional attachment such as a mixer and/or a pipetting machine.

EXAMPLE 8

Detailed Study on the Transient Response

A transient memory of 12 bit×4096 words was used to read and record the very rapid response signal generated by the inventive microbioelectrode.

Figure 13:
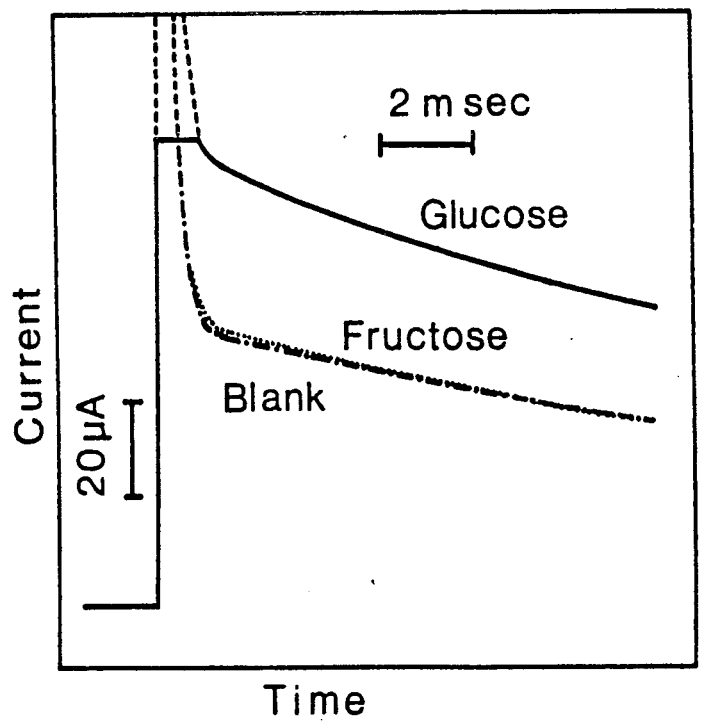
FIG. 13 is a graph showing closely a transient response as generated by the inventive microbioelectrode in the sensor of FIG. 9, where the response curves were measured by a transient memory.

The transient response upon the application of 0.6 volt versus Ag/AgCl reference electrode was recorded for glucose (20 mM), fructose (20 mM) and blank samples. Every response is shown in FIG. 13, which behaves a typical response caused by potential-application, i.e. the steep decay of charging current is followed by the gradual decrease of faradaic current. After the sufficient decay of capacitive (charging) current, the faradaic current was taken as a biosensing signal, i.e. after the rapid decay of the capacitive current, the faradaic current for hydrogen peroxide remained.

EXAMPLE 9

Measurement of Concentration by Transient Response Current

Figure 14:
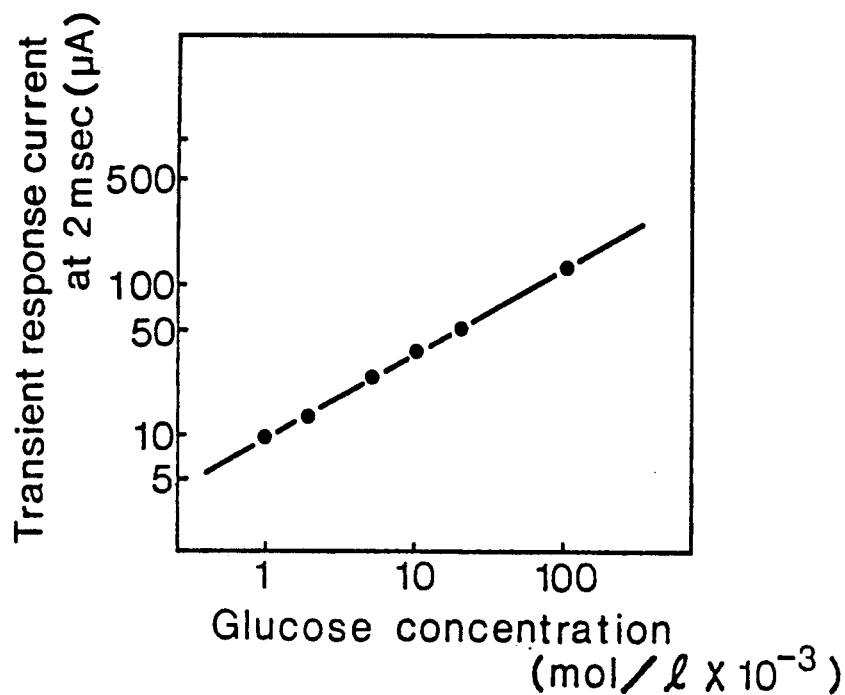
FIG. 14 is a graph showing the relation between glucose concentration and the sensor output (of which the transient response was measured by 2 milliseconds after the potential application), where the sensor output herein measured was the difference between the response for a glucose containing sample and the response for a blank sample.

The difference in output current between a glucose sample and a blank sample at the time of 2 microseconds after the application of a potential to the microelectrode versus the Ag/AgCl electrode was measured and plotted against the glucose concentration in a graph of FIG. 14.

A good linearity between the transient response and the glucose concentration is shown in FIG. 14.

Figure 15:
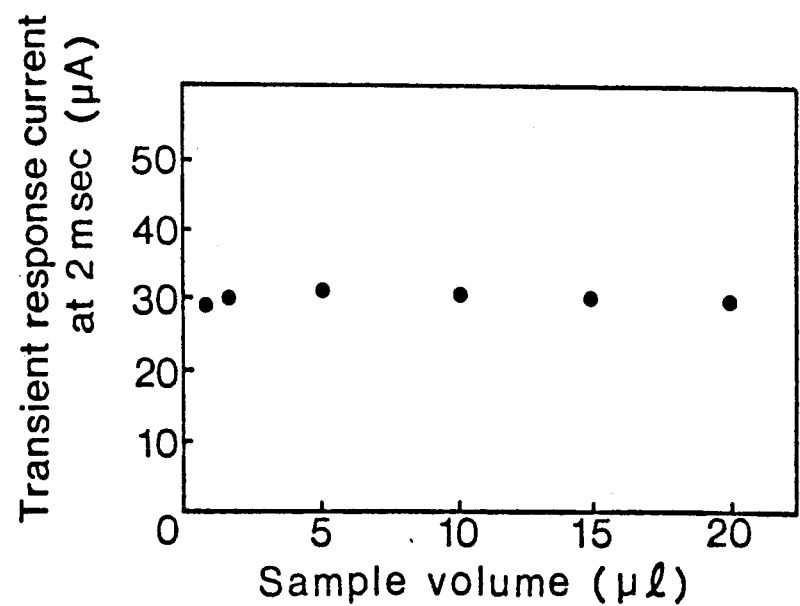
FIG. 15 is a graph showing the relation between the volume of the glucose containing samples and the sensor output measured at 2 milliseconds.

The response current was measured by changing the volume of the sample using the inventive microbioelectrode. The result is shown in FIG. 15. The coefficient of variation of the measured current was within 4% when n=10. It is revealed that the response current generated by the reaction in the biosensing device is independent of the sample volume to be loaded for the measurement.

EXAMPLE 10

Selectivity of Microbioelectrode

The Selectivity to a target substance in an amperometric measurement is dependent on the electronic reaction in the microbioelectrode. When the conventional noble metal electrode is used in an amperometric measurement, nonselective response occurs in the measurement of a sample which contains other saccharide and amino acid. When the microbioelectrode can be improved by forming an oxide of the noble metal to be used as a conductive layer for the electrode. Such surface oxide can be formed by polarizing anodically the matrix of the electrode with application of 1.2 V versus Ag/AgCl electrode for ten minutes.

Figure 16A:
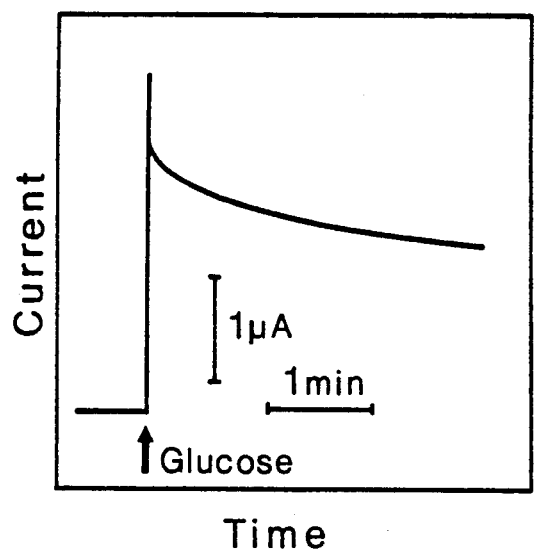
FIG. 16A and 16B are graphs showing a response curve measured by the inventive microbioelectrode which had been anodically polarized, upon the twice additions of fructose, galactose and glucose in this order, where the measurement was carried out in a batch system.
Figure 16B:
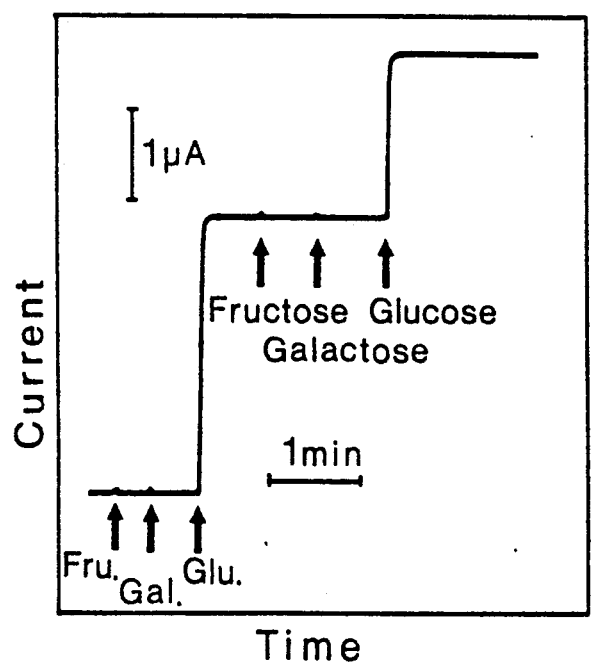

FIGS. 16A and 16B shows the response curves measured by using the microbioelectrode having glucose oxidase in its porous layer, which had treated with anodic polarization at 1.2 V for ten minutes. The response curve was obtained upon the sequential addition of fructose and galactose and glucose in this order.

FIGS. 16A and 16B evidences that the microbioelectrode responds significantly only to glucose and does not respond to fructose and galactose.

EXAMPLE 11

Improvement of Selectivity of Microelectrode for Flow Injection Analysis

Improvement of selectivity was found in a flow injection analysis using the assembly of FIGS. 4A and 4B.

Figure 17B:
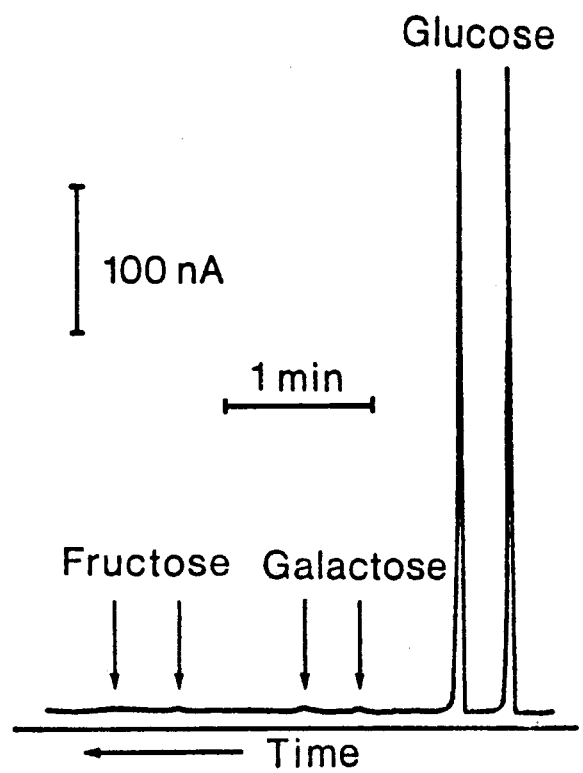
FIGS. 17A and 17B are graphs showing the nonselective responses to saccharides, measured by using the inventive microbioelectrode in a flow system, when the electrode had not been polarized after the deposition with the enzyme, and the improved selectivity of the response of the inventive microbioelectrode when it had been treated by an anodic polarization so as to improve the feature of the surface oxide of the inventive transducing platinized platinum electrode.
Figure 17A:
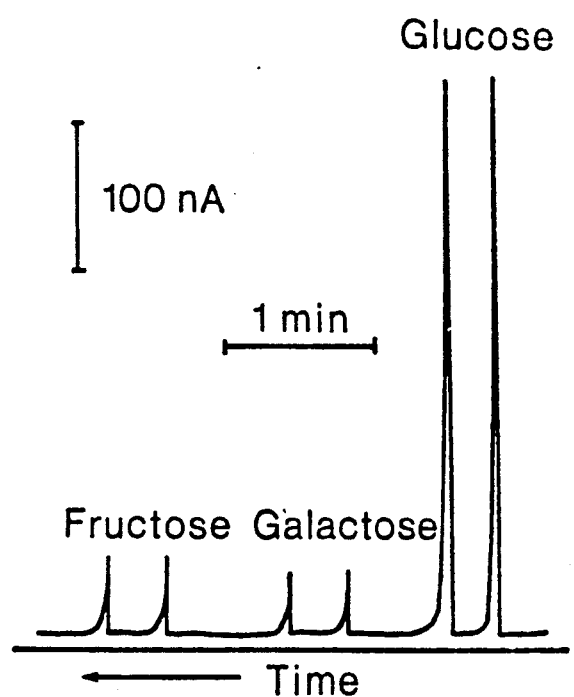

FIG. 17A shows the response curve measured, upon sequential addition of fructose, galactose and glucose in this order, by using the microbioelectrode which had been immobilized with glucose oxidase, which electrode had not been treated with anodic polarization and had been assembled in a transducing cell FIGS. 4A and 4B.

Next, the microbioelectrode was treated with anodic polarization, and then, the responsive curve was measured by such treated microbioelectrode, and the resulting response curve is shown in a graph of FIG. 17B.

FIGS. 17A and 17B reveal that the anodic polarization treatment in accordance with the present invention improve the selectivity of the microbioelectrode to the target substance (glucose) in measuring even in the presence of other saccharides than glucose. Therefore, it can be concluded that the inventive microbioelectrode is useful in the flow injection analysis.

As described in the foregoing, the inventive method of immobilizing a biologically active substance, the microbioelectrode prepared thereby, and an analytical method using the microbioelectrode can be used for a variety of measuring systems utilizing the biologically active substance, and further, in the system in which the microbioelectrode functions as a biosensing device, and is adopted not only for the measurement of physiologically active substance, but also for the fabrication of analytical instruments because the microbioelectrode exhibits extremely rapid response and high sensitivity.

We claim:

1. A microbioelectrode produced by direct immobilization of a biologically active substance on a surface of an electrically conductive material which comprises the steps of:
   (a) depositing fine particles of noble metal or a compound selected from the group consisting of platinum black, gold black, particulate rhodium oxide, palladium black and iridium black on the surface of an electroconductive material so as to form a porous conductive material or a conductive fine particle layer on said surface;
   (b) immersing the resulting porous conductive material or conductive fine particle layer in a solution containing an active substance so as to impregnate the active substance deeply into the conductive porous material or conductive fine particle layer; and
   (c) treating said porous conductive material or conductive fine particle layer by anodic oxidation.

2. The microbioelectrode as claimed in claim 1, wherein the microbioelectrode is formed by steps (a), (b) and (c) and further comprising the step of:
   (d) stabilizing the resulting active substance incorporated into the porous conductive material or conductive fine particle layer with a crosslinking agent.

3. The microbioelectrode as claimed in claim 2, wherein the microbioelectrode is formed by steps (a), (b), (c) and (d) and further comprising the step of:
 (e) forming a polymeric film on the surface of said conductive porous material or conductive fine particle layer for the stabilization of said active substance.

4. The microbioelectrode as claimed in claim 1, wherein said porous conducive material or conductive fine particle layer is treated by anodic oxidation after step (a).

5. A biologically active substance immobilized microbioelectrode comprising a fine particle electrically conductive surface layer incorporating an immobilized biologically active substance therein, formed by the steps of:
 (a) depositing fine particles of noble metal or a compound selected from the group consisting of platinum black, gold black, particulate rhodium oxide, palladium black and iridium black on a surface of an electroconductive material so as to form a porous conductive material or a conductive fine particle layer on said surface;
 (b) immersing the resulting porous conductive material or conductive fine particle layer in a solution containing said active substance so as to impregnate said active substance deeply into the conductive porous material or conductive fine particle layer; and
 (e) treating said porous conductive material or conductive fine particle layer by anodic oxidation.

6. The microbioelectrode as claimed in claim 5, wherein the microbioelectrode is formed by the steps (a), (b) and (c) and further comprising the step of:
 (d) stabilizing the resulting active substance incorporated into the porous conductive material or conductive fine particle layer with a crosslinking agent.

7. The microbioelectrode as claimed in claim 6, wherein the microbioelectrode is formed by steps (a), (b), (c) and (d) and further comprising the step of:
 (e) forming a polymeric film on the surface of said conductive porous material or conductive fine particle layer for the stabilization of said active substance.

8. The microbioelectrode as claimed in claim 5, wherein said porous conductive material or conductive fine particle layer is treated by anodic oxidation after step (a).

9. A method for immobilizing a biologically active substance within an electrically conductive material which comprises the steps of:
 (a) depositing fine particles of noble metal or a compound selected from the group consisting of platinum black, gold black, particulate rhodium oxide, palladium black and iridium black on a surface of an electroconductive material so as to form a porous conductive material or a conductive fine particle layer on said surface;
 (b) immersing the resulting porous conductive material or conductive fine particle layer in a solution containing said active substance so as to impregnate said active substance deeply into the conductive porous material; and
 (c) treating said porous conductive material or conductive fine particle layer by anodic oxidation.

10. The method as claimed in claim 9, further comprising the step of:
 (d) stabilizing the resulting active substance incorporated into the porous conductive material or conductive fine particle layer with a crosslinking agent.

11. The method as claimed in claim 10, further comprising the step of:
 (e) forming a polymeric film on the surface of said porous conductive material or conductive fine particle layer so as to stabilize said active substance.

12. The method as claimed in claim 9, wherein said porous conducive material or said fine particle layer is treated by anodic oxidation after step (a).

13. A microbioelectrode designed to have biologically active substances immobilized in the fine pores or on the surface of a porous conductive material or conductive fine particle layer which is deposited on the surface of a transducing electrode, wherein the porous conductive material or conductive fine particle layer consists of finely divided particles of noble metal or a compound selected from the group consisting of platinum black, gold black, particulate rhodium oxide, palladium black and iridium black, thereby having biological and electrochemical reactions occur simultaneously so as to enable direct transduction into an electric signal.

14. An analytical method of determining a physiological active substance which comprises:
 (a) measuring an electric signal generated when a given potential is applied by using a biologically active substance immobilized microelectrode as claimed in claim 1 as a functional electrode; and
 (b) determining a concentration of a target physiologically active substance by said generated electric signal.

15. The analytical method as claimed in claim 14, wherein the pulse potential is applied to said microbioelectrode, and a current at a transient response to the pulse potential is measured to determine a concentration of the target substance.

16. An analytical method of determining a physiologically active substance which comprises:
 (a) measuring an electric signal generated when a given potential is applied by using a biologically active substance immobilized microelectrode as claimed in claim 5 as a functional electrode; and
 (b) determining a concentration of a target physiologically active substance by said generated electric signal.

17. The analytical method as claimed in claim 16, wherein a pulse potential is applied to said microbioelectrode, and a current at a transient response to the pulse potential is measured to determine a concentration of the target substance.

18. A microbioelectrode produced by direct immobilization of a biologically active substance within a porous layer of precious metal material or compound found on a conductive substrate, which comprises the steps of:
 (a) depositing porous precious metal material or compound selected from the group consisting of platinum black, gold black, particulate rhodium oxide, palladium black and iridium black, on the surface of an electroconductive substrate, so as to form a layer of the porous precious metal material or compound of said surface;
 (b) immersing the resulting layer on said surface in a solution containing said biologically active substance so as to impregnate said active substance deeply in said layer; and (c) treating said layer by anodic oxidation.

19. The microbioelectrode in accordance with claim 18, wherein said solution further contains a cross-linking agent.

20. The microbioelectrode in accordance with claim 18, further comprising the step of:

(d) forming a polymeric film on the surface of said layer for the stabilization of said active substance.

* * * * *